United States Patent [19]

Sterling

[11] Patent Number: 5,030,632

[45] Date of Patent: Jul. 9, 1991

[54] LOW DOSE TEMAZEPAM

[75] Inventor: William R. Sterling, Pine Brook, N.J.

[73] Assignee: Sandoz Pharm. Corp., E. Hanover, N.J.

[21] Appl. No.: 569,787

[22] Filed: Aug. 17, 1990

Related U.S. Application Data

[63] Continuation of Ser. No. 434,142, Nov. 9, 1989, abandoned, which is a continuation of Ser. No. 295,332, Jan. 10, 1989, abandoned, which is a continuation of Ser. No. 910,571, Sep. 23, 1986, abandoned.

[51] Int. Cl.$^5$ ............................ A61K 9/14; A61K 9/48
[52] U.S. Cl. ..................................... 514/221; 424/451; 424/452; 424/489; 514/923; 514/962
[58] Field of Search ............... 514/221, 923, 962; 424/451, 452, 489

[56] References Cited

U.S. PATENT DOCUMENTS

| | | | |
|---|---|---|---|
| 3,152,045 | 10/1964 | Vance et al. | 514/221 |
| 3,867,529 | 2/1975 | Ferrari et al. | 514/221 |
| 4,151,273 | 4/1979 | Riegelman et al. | 424/78 |
| 4,166,800 | 9/1979 | Fong | 424/497 |
| 4,232,016 | 11/1980 | Poetsch et al. | 514/221 |
| 4,261,987 | 4/1981 | Schlager | 514/221 |
| 4,316,897 | 2/1982 | Lotz | 514/221 |
| 4,384,975 | 5/1983 | Fong | 424/497 |
| 4,399,129 | 8/1983 | Gowers et al. | 514/221 |
| 4,479,911 | 10/1984 | Fong | 424/497 |
| 4,665,086 | 5/1987 | Short | 514/416 |
| 4,666,903 | 5/1987 | Gallager | 514/220 |
| 4,685,918 | 8/1987 | Amidon et al. | 424/467 |
| 4,721,709 | 1/1988 | Seth et al. | 514/221 |
| 4,780,316 | 10/1988 | Brox | 424/456 |
| 4,933,105 | 6/1990 | Fong | 424/497 |
| 4,940,588 | 7/1990 | Sparks et al. | 424/490 |
| 4,952,402 | 8/1990 | Sparks et al. | 424/419 |

FOREIGN PATENT DOCUMENTS

| | | | |
|---|---|---|---|
| 953102 | 3/1964 | United Kingdom | 514/221 |
| 2067403A | 7/1981 | United Kingdom | 514/221 |
| 2142824A | 1/1985 | United Kingdom | 514/221 |

OTHER PUBLICATIONS

Br. J. Clin. Pharm. (1976), 3,543–550, Nicholson et al.
La Riforma Medica, 16:425–427, 1970, Senini et al.
Bombay, Hosp. J, 16:222–223, 1974, Sardesai et al.
Neuropsychobiology, 9(1):52–65, 1983, Matejcek et al.
Sarteschi et al., C.A. 77:772t (1972).
Bittencourt et al., C.A. 92:33698m (1980).
Hindmarch, C.A. 91:83557q (1979).
Fuccella, C.A. 92:47189h (1980).
Patrick et al., C.A. 108:68825b (1988).
Mattila et al., C.A. 103:166033h (1985).
Salonen et al., C.A. 104:136001z (1986).
Roth et al., C.A. 92:15829a (1980).
Fucella, C.A. 90:78856g (1979).
Laffont et al., C.A. 98:119578h (1983).
Borbely et al., C.A. 100:96533h (1984).
Okuma et al., C.A. 97:65862e (1982).

*Primary Examiner*—Shep K. Rose
*Attorney, Agent, or Firm*—Gerald D. Sharkin; Robert S. Honor; Thomas O. McGovern

[57] ABSTRACT

This invention relates to a hard gelatin capsule containing no more than 5 to 10 milligrams of crystalline temazepam and its use in the treatment of transient insomnia.

3 Claims, No Drawings

LOW DOSE TEMAZEPAM

This is a continuation of application Ser. No. 07/434,142, filed Nov. 9, 1989, now abandoned which in turn is a continuation of application Ser. No. 07/295,332, filed Jan. 10, 1989, now abandoned, which in turn is a continuation of application Ser. No. 06/910,571, filed Sept. 23, 1986, now abandoned.

This invention relates to a new pharmaceutical form of temazepam and its use as a hypnotic agent.

More particularly, it relates to a low dose hard gelatin temazepam capsule and its use in the treatment of insomnia, especially, transient insomnia.

Temazepam, whose chemical name is 7-chloro-1,3-dihydro-3-hydroxy-1-methyl-5-phenyl-2H-1,4-benzodiazepin-2-one is a well known hypnotic agent used in the treatment of insomnia. The commercial product is sold in the United States in the form of hard gelatin capsules containing 15 and 30 milligrams of temazepam. Soft gelatin capsules containing 10 and 20 milligrams of temazepam are also available abroad. The hard gelatin capsule has been studied in great depth and has been found to be generally effective at doses of 15 and 30 milligrams of temazepam. At doses of 10 and 20 milligrams, the soft gelatin capsules have also been found to be effective, although Nicholson, et al. (Br. J. Clin. Pharmac., 3,543–550,1976) have reported that at 10 milligrams, no change in total sleep time was found, whereas at 20 milligrams, total sleep time was markedly increased. Lower dose forms of temazepam containing 5 milligrams of the compound have been used in a number of investigations (LaReforma Medica, 16,425–427, 1970; Bombay Hosp. J., 16,222–223,1974; Neuropsychobiology 9(1),52–65,1983) but have never been found to be useful in treating insomnia. In the Neuropsychobiology publication, the authors indicate that at 5 milligrams, temazepam is known to be of no clinical importance as a hypnotic agent.

Although the side effects of temazepam are minimal, the lowest effective dose of the product would be desirable. It would be especially useful in treating transient insomnia, which occurs in healthy individuals whose sleep pattern has been temporarily disrupted, for example by airplane travel or by changing work shifts. It has now been found that a hard gelatin capsule comprising up to 10 milligrams of temazepam, in which the temazepam particles have a specific surface area of from 0.65 to 1.1 square meters per gram ($m^2/g$) and 95% of the particles have a particle size diameter of less than 65 microns (u), is effective in the treatment of insomnia, especially in improving sleep latency. Preferably the capsule contains the temazepam in amounts of from 5 to 10 milligrams, more preferably 6 to 8 milligrams, especially 7.5 milligrams, in combination with a pharmaceutically acceptable carrier. The capsule is normally administered just before bedtime.

Crystalline temazepam can be synthesized with a purity of not less than 98% using known procedures such as that disclosed in U.S. Pat. No. 3,296,245. The bulk temazepam is milled to obtain the required particle size and surface area with an Alpine 160 UPZ mill using a stainless steel pin. The particle size is determined using a Malverne Particle Sizer, Model 3600 E equipped with a 14.3 mm flow cell and a 100 mm lens. Surface area measurements are made essentially in accordance with the standard B.E.T. procedure of Brunauer, Emmet and Teller (J. Am. Chem. Soc. 59, 2682, 1937 and J. Am. Chem. Soc., 60, 309, 1938). The temazepam is formulated with standard hard gelatin capsule excipients and encapsulated in conventional hard gelatin capsules using known procedures.

The use of low dose temazepam hard gelatin capsules in the treatment of transient insomnia was evaluated in a double blind, parallel group, placebo-controlled sleep laboratory study using 201 healthy subjects. Just before bedtime each subject was given a capsule containing placebo, or 7.5, 15 or 30 milligrams of temazepam. The number of subjects in the four treatment groups were placebo — 50; 7.5 milligrams — 51; 15 milligrams — 49; and 30 milligrams — 51. Testing was carried out over a period of one night in the sleep laboratory. The key parameters of sleep latency and total sleep time were among those measured by EEG analysis (polysomnography). The mean values for sleep latency and total sleep-time obtained with each treatment group were as follows:

| Group | Sleep Latency (min.) | Total Sleep Time (min.) |
|---|---|---|
| Placebo | 37 | 411 |
| 7.5 m.g. | 26 | 422 |
| 15 m.g. | 22 | 429 |
| 30 m.g. | 18 | 441 |

As can be seen from the above data 7.5 milligrams of temazepam was effective in reducing both sleep latency and increasing total sleep time in the study. The most unexpected result is that the effect occurred as the dosage dropped below the 15 milligram dosage level. The usual effect-no effect results, which would have been expected between 7.5 and 15 milligrams of temazepam based on previous hard gelatin capsule studies did not occur.

EXAMPLE 1

White crystalline temazepam having a purity of not less than 98% is prepared according to the procedure described in U.S. Pat. No. 3,296,245. The bulk temazepam obtained is fed into an Alpine 160 UPZ mill with a stainless steel pin at a rate of about 40 kilograms (kg) per hour using a mill speed of about 11,000 RPM to obtain temazepam particles having a specific surface area of 0.65 to 1.1 $m^2/g$ area and 95% of the particles having a particle size diameter of less than 65 u. The surface area measurement is made with the Quantector Gas Flow System and Quantasorb Surface Area Analyser at the temperature of liquid nitrogen ($-196°$ C.) using krypton as the absorbant and helium as the carrier gas. The particle size diameter is determined with the Malverne Particle Sizer at an obscuration value of 0.2 to 0.25 using a 0.1% Tween 80 solution in water saturated with temazepam in which 1 to 2 grams of temazepam sample to be tested have been dispersed. After the feed rate and mill speed of the Alpine mill have been set, they are monitored at regular intervals to maintain the required particle size and surface area.

EXAMPLE 2

To prepare hard gelatin capsules containing 7.5 milligrams of the temazepam of example 1, 12 kg of temazepam and 12 kg. of lactose are passed through an 18 mesh screen. This mixture is added to 372 kg of lactose, which has also been passed through an 18 mesh screen, and 4 kg of magnesium stearate in a 30 cu. ft. PK Mixer without an intensity bar. The capsule ingredients are mixed for 30 minutes using tumbling action only. The capsule mix is encapsulated in number 3 Lock hard gelatin capsules with opaque blue caps and opaque pink bodies, and the capsules are then passed through a capsule polisher. Each capsule contains 250 milligrams of capsule mix and 7.5 milligrams of temazepam.

I claim:

1. A method of treating transient insomnia with temazepam in a human in need of said treatment the improvement which consisting essentially of the step of administering to said human a hard gelatin capsule containing not more than 5 to 10 milligrams of crystalline temazepam having a surface area of from 0.65 to 1.1 $m^2/g$ and 95% of the temazepam having particle size diameters of less than 65 microns.

2. A method according to claim 1, in which 6 to 8 milligrams of temazepam are administered.

3. A method according to claim 1 in which 7.5 milligrams of temazepam are administered.

* * * * *